United States Patent [19]

Carduner et al.

[11] Patent Number: 5,129,257

[45] Date of Patent: Jul. 14, 1992

[54] SYSTEM FOR MEASURING ENGINE EXHAUST CONSTITUENTS

[75] Inventors: Keith R. Carduner, Dearborn; Alex D. Colvin, Oak Park; Dick Y. W. Leong, Bloomfield Hills, all of Mich.

[73] Assignee: Ford Motor Company, Dearborn, Mich.

[21] Appl. No.: 633,925

[22] Filed: Dec. 26, 1990

[51] Int. Cl.$^5$ .................................................. G01M 15/00
[52] U.S. Cl. ........................................ 73/116; 73/23.31
[58] Field of Search ............... 73/116, 23, 31, 31.05, 73/23.2, 863.02, 863.03

[56] References Cited

U.S. PATENT DOCUMENTS

| | | |
|---|---|---|
| 3,473,372 | 10/1969 | Klink . |
| 3,606,155 | 9/1971 | Morris et al. . |
| 3,928,162 | 12/1975 | Takata . |
| 4,029,563 | 6/1977 | Binder et al. . |
| 4,277,368 | 7/1987 | Amy et al. . |
| 4,357,828 | 11/1982 | Nakano . |
| 4,409,069 | 10/1983 | Luft . |
| 4,499,190 | 2/1985 | Spicer et al. . |
| 4,506,337 | 3/1985 | Yasuhara . |
| 4,586,367 | 5/1986 | Lewis . |
| 4,622,105 | 11/1986 | Liu et al. . |
| 4,638,658 | 1/1987 | Otobe . |
| 4,677,847 | 7/1987 | Sawatari et al. . |
| 4,706,193 | 11/1987 | Imajo et al. . |
| 4,727,746 | 3/1988 | Mikasa et al. . |
| 4,742,476 | 5/1988 | Schwartz et al. . |

FOREIGN PATENT DOCUMENTS 2051354 1/1981 United Kingdom .................. 73/116

OTHER PUBLICATIONS

SAE Technical Paper Series 871913 "Real-Time Measurement of Engine Oil Economy".

Primary Examiner—Robert Raevis
Attorney, Agent, or Firm—Jerome R. Drouillard; Clifford L. Sadler

[57] ABSTRACT

A system for measuring an automotive engine exhaust constituent includes a meter for measuring the mass of air flowing through the engine and for generating a flow signal corresponding to the airflow, and a sample handling apparatus for separating a fraction of the exhaust flowing through the engine and for conducting the exhaust fraction to an analyzer. The system further includes diluent adding means for doping the extracted exhaust fraction with a diluent gas upstream of the analyzer and a processor for receiving the mass flow signal from the engine mass flow meter and for operating the diluent adding device in response to the flow signal. The processor operates the diluent valve such that the flow rate of exhaust gas into the analyzer remains a relatively constant fraction of the total exhaust flowing from the engine.

22 Claims, 2 Drawing Sheets

SYSTEM FOR MEASURING ENGINE EXHAUST CONSTITUENTS

BACKGROUND OF THE INVENTION

1. Field of the Invention

This invention is related to an instrument for measuring trace constituents in the flow of exhaust from automotive engines. An instrument according to this invention is particularly well-suited for the measurement of engine oil consumption, as determined by the presence of combustion species attributable to chemical compounds contained in lubricating oil.

It is desirable for engine manufacturers to have a means for quickly determining engine oil consumption, because oil usage is important, not only for reasons of customer satisfaction, but also as a measure of basic engine integrity.

2. Disclosure Information

Many methods have been proposed for measurement of engine oil consumption. U.S. Pat. No. 3,473,372 to Klink discloses a system which uses a calibrated measuring vessel for determining oil usage. Such a system is hardly much of an improvement over the oldest known methods for measuring oil consumption in which the engine being tested was merely operated for an extended period of time sufficient to allow weighing or volume measurement techniques to determine, albeit with mediocre accuracy, the engine's oil consumption.

Engine designers have sought improved ways for measuring engine oil consumption for many years. One such alternative has involved the measurement of trace compounds in the engine exhaust. For example, a radiometric method involves the addition of a radioactive tracer to the oil, with the tracer being tracked in the engine's exhaust. This technique suffers from the drawback that it requires synthesis and addition of the radioisotope tagging compound, which renders the technique generally unsuitable for routine use.

Another method for determining engine oil usage involves the measurement of an oil additive, such as zinc dialkyldithiophosphate. Such a method is disclosed in U.S. Pat. No. 4,321,056 to Dimitroff. A sample of the exhaust gas in the engine is passed through a condenser in order to condense zinc sulphate in the exhaust. After the sample is treated, it is passed through a coulometer cell wherein a reading is obtained which is proportional to the engine oil consumed during the sampling period. This system, unfortunately, is incapable of giving a real time measurement of engine oil consumption.

Analytical systems for sampling exhaust gases for the purpose of determining the mass emission of various constituents have generally drawn the total exhaust flow through the system and combined the exhaust with make-up air so that the mass emission of a particular constituent could be determined notwithstanding that the mass flow through the engine being tested varied widely with time while the engine was being operated according to an unsteady cycle. U.S. Pat. No. 3,603,155 to Morris et al., U.S. Pat. No. 4,586,367 to Lewis, and U.S. Pat. No. 4,727,746 to Mikasa et al. all disclose systems in which all of the exhaust gases from a vehicular engine are drawn into the sample handling system of an analyzer. Such systems are undesirable from the standpoint that they require very large machines for handling and chilling the large volume of exhaust gases emanating from larger engines.

It is an advantage and object of the present invention that a system for measuring exhaust constituents according to this invention will operate by drawing into the machine only a small fraction in total exhaust flowing from the engine. As a result, the present instrument obviates the need for large air handling and chilling machines.

An instrument according to the present invention may beneficially use a coulometer as a detector for the exhaust constituent being measured. Electrochemical cells for measuring trace chemical constituents are disclosed in U.S. Pat. No. 3,928,162 to Takata, U.S. Pat. No. 4;029,563 to Binder et al., U.S. Pat. No. 4,409,069 to Luft and U.S. Pat. No. 4,622,105 to Liu et al. None of these cells is suitable for the continuous measurement of sulphur dioxide or any other trace element carried in the stream of exhaust coming from an engine, on a real time basis.

U.S. Pat. No. 4,277,368 to Amy et al. and U.S. Pat. No. 4,499,190 to Spicer et al. disclose coulometric and fluorescent techniques for detecting sulphur dioxide. As with the previously noted coulometric methods, these methods are not suitable for measuring sulphur dioxide in a flowing exhaust stream from an engine in real time because they lack adequate time response characteristics.

*SAE Technical Paper Series* 871913 entitled "Real-Time Measurement of Engine Oil Economy", which is hereby incorporated by reference in this disclosure, discloses a real time microcoulometric cell. The present invention uses a similar cell but also includes computer control for valves which operate various functions associated with the cell, as well as automatic introduction of electrolyte and calculation of the engine oil consumed by computer.

It is a further object of the present invention to provide an instrument using a coulometric cell powered by an electronic circuit which allows the cell to work in real time.

Other objects, features and advantages of an analyzer system according to the present invention will become apparent to the reader of this specification.

SUMMARY OF THE INVENTION

A system for measuring an automotive engine exhaust constituent comprises a meter for measuring the mass of air flowing through the engine and for generating a flow signal corresponding to the airflow, and sample handling apparatus for separating a fraction of the exhaust flowing from the engine and for conducting the exhaust fraction to an analyzer. This system further includes diluent adding means for doping the exhaust fraction with diluent gas upstream of the analyzer, and processor means for receiving the flow signal and for operating the diluent adding means in response to the flow signal. A meter for measuring air flow may comprise an airflow sensor associated with an electronic engine control for operating a fuel injection system engine or a free-standing flow meter, which measures the mass of air flowing through the engine.

A sample handling apparatus according to the present invention preferably comprises a sample line powered by a vacuum pump and a mass flow meter for metering flow through the sample line, with the mass flow meter preferably being situated upstream of the vacuum pump.

The diluent adding means preferably comprises a source of diluent gas, a flow meter for measuring the flow of diluent and for generating a diluent signal which corresponds to the magnitude of the flow, and a diluent valve for controlling the flow of the diluent gas introduced in the sample handling apparatus, with the diluent valve being operated by a processor in response to the diluent signal and to the flow signal generated by the airflow meter measuring the mass of air flowing through the engine.

The processor operates the diluent valve such that the mass of exhaust flowing into the analyzer remains at a relatively constant fraction of the total exhaust flow.

The analyzer means incorporated in an instrument according to the present invention preferably comprises means for detecting a constituent in the exhaust conveyed to the analyzer by the sample handling apparatus, means for generating a constituent signal corresponding to the detected level of a constituent, and means for transmitting the constituent to the processor.

A system according to the present invention may beneficially be used for measuring the mass flow of sulphur dioxide in an automotive engine exhaust. In this case, the analyzer will be specifically adapted for detecting the level of sulphur dioxide in the exhaust and will include not only a detector but also means for promoting oxidation of the exhaust fraction flowing through the analyzer. The detector means will determine the mass flow rate of sulphur dioxide in the sampled exhaust flow. The detector or analyzer will further include means for generating a sulphur dioxide signal corresponding to the detected level of sulphur dioxide. This constituent signal will comprise a current signal with the magnitude of the current being proportional to the concentration of sulphur dioxide in the exhaust. The detector preferably comprises an electrochemical cell, specifically a coulometric cell. In this case, the cell is preferably equipped with a pump system for automatically controlling the quantity of electrolyte within the cell.

According to yet another aspect of the present invention, a method for using an analyzer to determine the amount of lubricating oil consumed by an automotive engine comprises the steps of:

(a) determining the amount of sulphur dioxide in the room air being drawn into the engine;

(b) maintaining a constant total flow through the analyzer comprised of a constant fraction of the engine's exhaust gas and a diluent gas through the analyzer, while:

(c) determining the amount of sulphur dioxide contained within the engine's exhaust while adding a known quantity of sulphur dioxide to the engine's intake air supply while the engine is operating;

(d) determining the amount of sulphur dioxide contained within the engine's exhaust while operating the engine on room air;

(e) determining an efficiency factor for the analyzer by comparing the amounts of sulphur dioxide determined in Steps (c) and (d); and (f) using the efficiency factor and the amounts of sulphur dioxide determined in steps (a) and (d) and the sulfur content of the oil to determine the amount of lubricating oil leaving the engine through its exhaust.

DETAILED DESCRIPTION OF THE PREFERRED EMBODIMENTS

Figure 1:
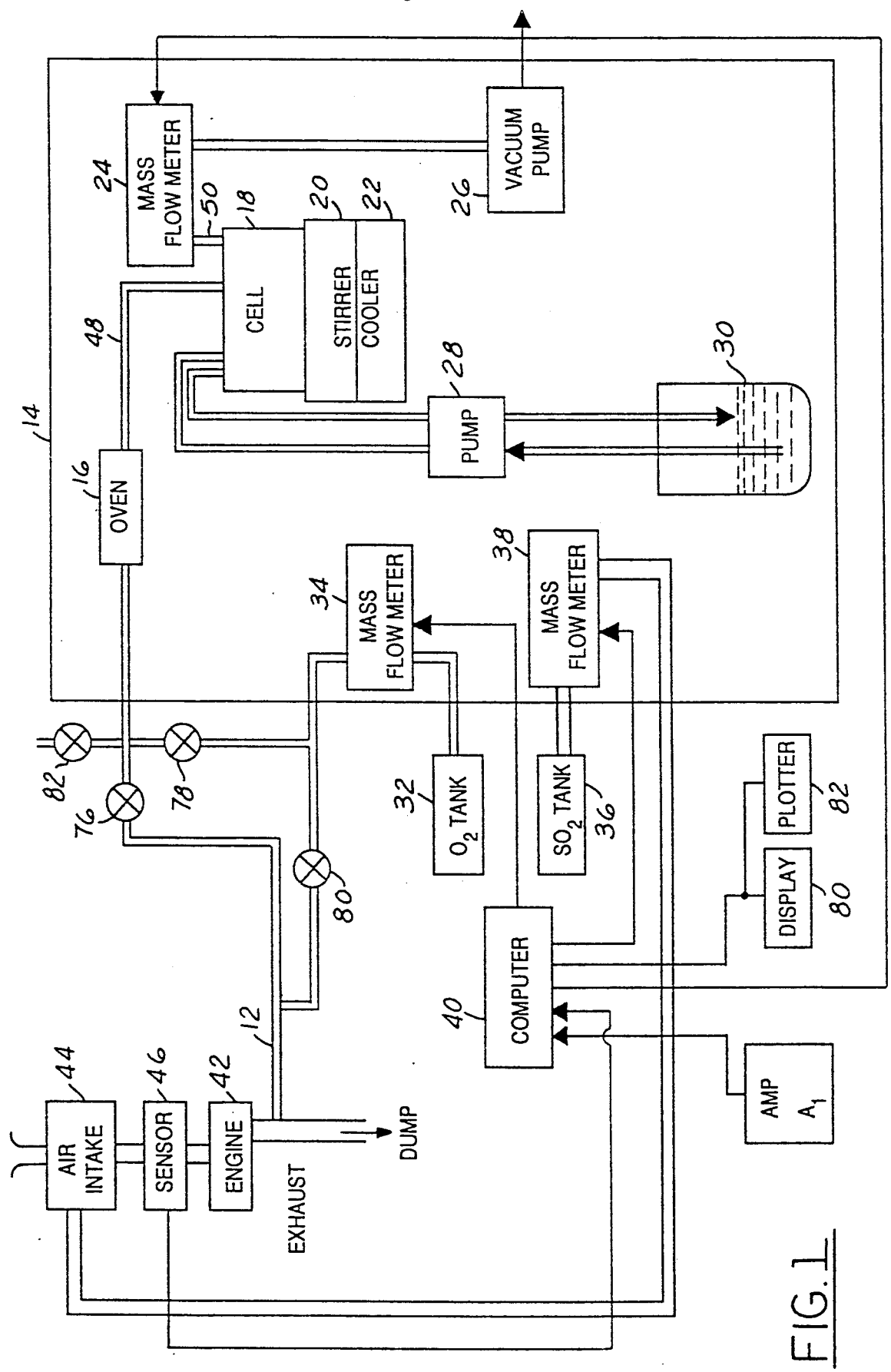
FIG. 1 is an overall block diagram of a system according to the present invention.

As shown in FIG. 1, an engine 42, having a mass flow sensor 46, for determining the air flowing through the intake of the engine 44, has a portion of the exhaust of the engine split off into sample line 12. Mass flow sensor 46 may comprise either a conventional mass flow sensor associated with an electronic fuel injection system of engine 42 or, alternatively, the sensor could comprise a laminar flow element or other type of sensor known to those skilled in the art and suggested by this disclosure. For example, the airflow could be calculated from measured fuel flow and air/fuel ratio. In any event, mass flow sensor 46 generates a flow signal corresponding to the airflow through engine 42 and sends this information to computer 40. The sample of exhaust passing through heated sample line 12 is doped with diluent from diluent tank 32, which passes through diluent flow meter 34 according to the commands of computer 40. In the event that an analyzer according to the present invention is intended to detect sulphur dioxide in the engine's exhaust, the diluent may be oxygen, which is useful to promote the complete combustion of reactive material in the exhaust so that there is no reactble material received by chemical cell 18. Heated sample line 12 is preferably held to a temperature of approximately 500° Centigrade. After traversing the sample line, the sample passes through hot box 14, which is held at 110° Centigrade.

Moving through hot box 14, the sample first passes through oven 16 which completes the oxidation of hydrocarbon. The oven is held at about 1000° Centigrade. If desired, the oven could be equipped with a catalytic convertor. Leaving the oven, the doped exhaust gas passes through inlet tube 48 and then into cell 18. The cell illustrated in FIG. 1 comprises a coulometer cell, the operation of which will be explained in another part of this specification.

During exhaust emission studies performed with the present system while an engine is operating at a steady state, the flow rate of diluent oxygen is maintained at a constant value. During cyclical or transient engine operation, the amount of oxygen or other diluent is varied in inverse proportion to the mass flow of air into the engine with the combined mass of exhaust and diluent flowing in sample line 12 remaining a constant.

After flowing through cell 18, the sample passes out of the cell through outlet tube 50 and then through sample flow meter 24, and vacuum pump 26, before being discharged from the instrument. Sample flow meter 24 is Placed upstream from vacuum pump 26 so that leaks, if any, in vacuum pump 26 will not affect the accuracy of the measurement made by the sample flow meter.

As is further shown in FIG. 1, cell 18 is equipped with pump 28 and electrolyte reservoir 30 for maintaining the electrolyte at an appropriate level within the cell. Pump 28 could comprise a peristaltic pump or other type of pump known to those skilled in the art and suggested by this disclosure. Cell 18 is further equipped with stirrer 20 and cooler 22. The cooler could comprise a thermoelectric cooler or some other type of cooler known to those skilled in the art and suggested by this disclosure.

In addition to diluent provided by diluent tank 32 and diluent flow meter 34, the composition of the exhaust flow will be altered by gas from sulphur dioxide tank 36 and sulphur dioxide flow meter 38. Under command of computer 40, the sulphur dioxide tank and flow meter Provide additional sulphur dioxide to the air intake of the engine. The usage of this additional sulphur dioxide will be explained below.

Figure 2:
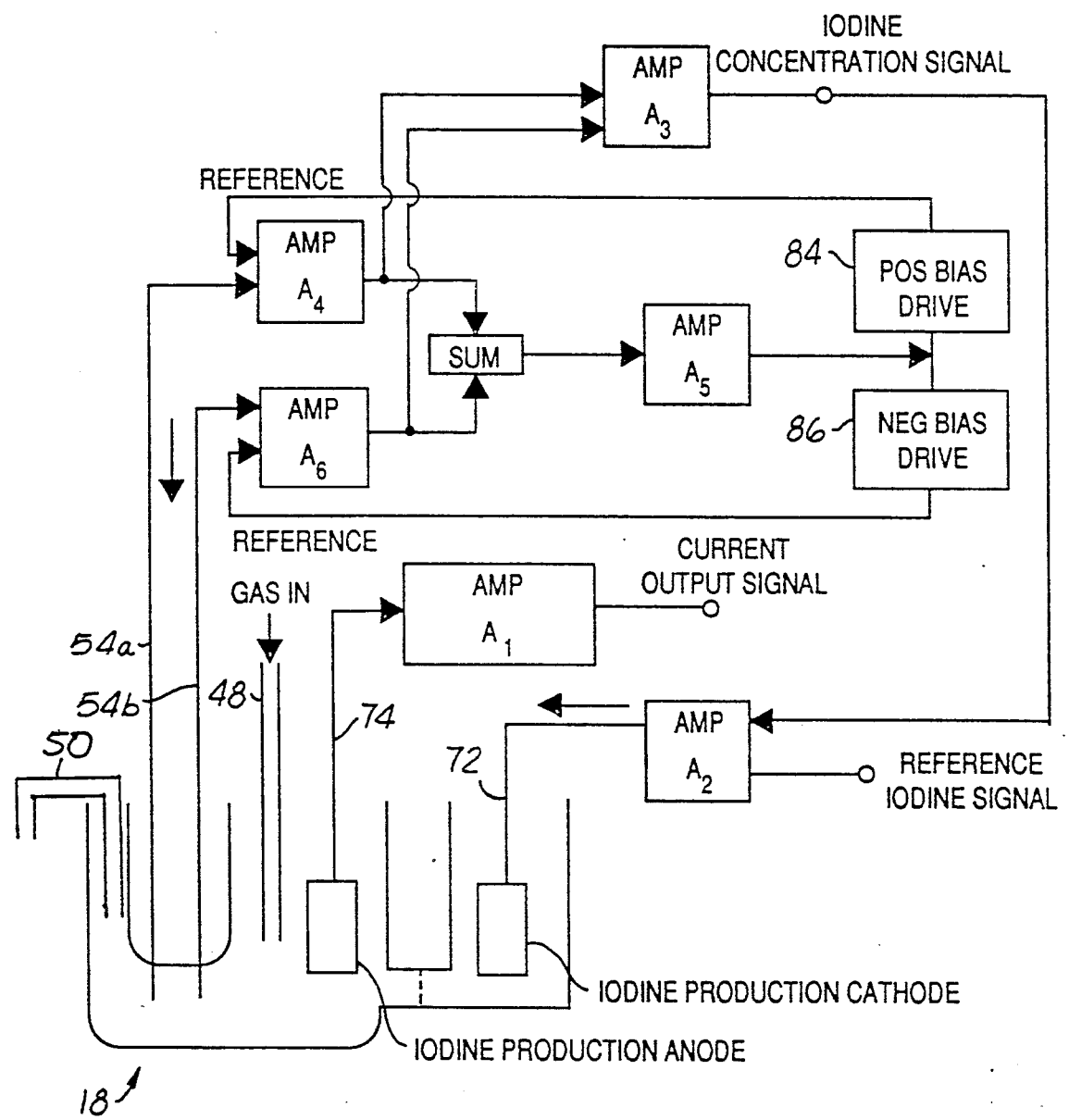
FIG. 2 is a block diagram of a coulometer and associated electronics of a system according to the present invention.

A schematic of the coulometric cell and associated electronics is shown in FIG. 2. Cell 18 is equipped with a pair of platinum iodine concentration electrodes 54a and 54b. Sulphur dioxide in the sample gas passing through the cell by means of inlet tube 48 and outlet tube 50 is oxidized according to the following equation:

$$SO_2 + I_3^- + 2H_2O \rightarrow SO_4^= + 3I^- + 4H^+$$

Potassium iodide (KI) present in the cell's electrolyte provides the iodine. Electrodes 54a and 54b continuously provide a current signal that is directly proportional to the $I_3^-$ concentration. Electrodes 54a and 54b comprise two platinum wires immersed in the electrolyte. A small voltage on the order of 40 millivolts is maintained between the electrodes. The current passing between the two electrodes is a measure of the iodine concentration in the cell's electrolyte. Amplifiers $A_4$, $A_5$ and $A_6$ act to maintain the 40 millivolt difference between electrodes 54a and 54b. In so doing, amplifiers $A_4$ and $A_6$ act as current to voltage converters. If the current Passing through electrodes 54a and 54b is not equal, then the output of an average bias drive, amplifier $A_5$ is non-zero. The output of amplifier $A_5$ is processed by positive bias drive 84 and negative bias drive 86. Accordingly, an appropriate offset occurs on the reference inputs to amplifiers $A_4$ and $A_6$ which will equalize the current. This assures that there are no stray currents in the cell which are unrelated to the $I_3^-$ concentration. Amplifier $A_3$ is a difference amplifier which compares the outputs of amplifiers $A_4$ and $A_6$, with the difference being proportional to the detector current flowing between electrodes 54a and 54b. Of course, the detector current is proportional to the $I_3^-$ concentration. Amplifier $A_3$ generates a current for input to amplifier $A_2$ with the current being proportional to the difference between the outputs of amplifier $A_4$ and $A_6$ Amplifier $A_2$ compares the output of amplifier $A_3$ with the measured reference value. If the current of amplifier $A_3$ is less than the reference, then the difference is used to produce a current through cell 18 from iodine production cathode 72 to iodine production anode 74 which produces iodine in the cell by the following equation:

$$3I^- \rightarrow I_3^- + 2e^-$$

Amplifier $A_1$ is a current to voltage converter attached to the iodine production anode. This amplifier measures the flow of current used to generate $I_3^-$. The current flow will generate just enough $I_3^-$, to make up for the amount used up according to the first equation listed above. The current is directly related to, and therefore a measure of, the $SO_2$ entering the cell.

During steady state engine operation, three levels of coulometer reading need to be determined to compute oil consumption. To begin the test, valves 76 and 80 are closed and valves 78 and 82 are open (FIG. 1), allowing oxygen to flow from tank 32 and flowmeter 34 into cell 18, along with room air. The signal level output, as conveyed by amplifier $A_1$ to computer 40, is recorded by the computer as value AS1. This corresponds to a room air, or background level of $SO_2$. The second step begins with the opening of valves 76 and 80 and the closing of valve 78. The signal from amplifier $A_1$ will now include the current due to the flow of $SO_2$ which originated with the lubricating oil. This is signal AS2. Finally, without changing the valves, a small amount of sulphur dioxide is introduced into air intake 44 from $SO_2$ tank 36 and $SO_2$ flowmeter 38. The current from the coulometer, which is termed AS3, includes $SO_2$ both from oil consumed by the engine and from sulphur dioxide added to air intake 44. Oil consumption in grams of oil per hour of engine operation (GM) may be calculated by computer 40 as follows:

$$GM = K*SG/(AS3-AS2)*(AS2-AS1)/SO,$$

where K is a known constant; SG is the sulphur dioxide flow from the sulphur dioxide tank in cc/min; SO is the weight percent sulphur in oil; and AS1, AS2 and AS3 are defined above and are in units of microamperes. The results of the calculation may be read on either display 80 or plotter 82.

The procedure for determination of transient oil consumption will now be described.

During transient engine operation, airflow through the engine changes rapidly. In order to assure that the output of cell 18 accurately reflects the concentration of the measured constituent in the exhaust, in this case $SO_2$, the mass fraction of the total flow through the analyzer contributed by the exhaust gas must be proportional to the mass flow through the engine itself. In other words, when the exhaust flow increases, the proportion of the total analyzer flow which is comprised of the exhaust flow must correspondingly increase. The analyzer handles this problem by functioning essentially as a constant volume sampler, with the total flow through the coulometer cell being held constant by sample flow meter 24. Diluent gas flow is determined according to the following equation:

$$TDOF = TF - K*EAF$$

where TDOF is the transient dilution oxygen flow, TF is the total sample flow, K is a constant, and EAF is the engine air flow as measured by mass flow sensor 46. It may seem from the equation above that the dilution air flow increases as the engine air flow decreases, and vice versa. For example, if the engine air flow is zero, then the total flow through the instrument is entirely comprised of dilution oxygen. If, on the other hand, the engine air flow is at its maximum point, the dilution flow of oxygen will be at its minimum value. In this manner the exhaust flow through the analyzer will be maintained at a constant fraction of the total exhaust flow form the engine.

In transient operation, the oil consumption measurement is comprised of three steps. During the background step, valves 76 and 80 are closed and 78 and 82 are open and a mixture of room air and dilution oxygen is sampled. During engine phase, the engine is operated through one or more transient cycles on a dynamometer and the output of cell 18 is taken into memory by computer 40. Finally, the engine is operated through an identical cycle, while $SO_2$ is added to air intake 44 through $SO_2$ tank 86 and $SO_2$ flow meter 38. The difference between the average coulometer readings in the phases where the engine is operated with and without added $SO_2$ are used to calibrate the coulometer. The difference between the coulometer readings during the engine operation phase without $SO_2$ and in the background phase are used to calculate the total oil consumption during the transient cycle. The difference between the coulometer output current at any point during a transient cycle and the background current is used for calculating instantaneous oil consumption.

The engine $SO_2$ signal at any point during transient operation is directly proportional to oil consumption, but is delayed a few seconds by the coulometer response. Accordingly, the previously described equation for calculating oil consumption may be employed.

While the invention has been shown and described in its preferred embodiments, it will be clear to those skilled in the arts to which they pertain that many changes and modifications may be made thereto without departing from the scope of the invention.

We claim:

1. A system for measuring an automotive engine exhaust constituent, comprising:
   a meter for determining the mass of air flowing through said engine and for generating an engine airflow signal corresponding to said airflow;
   sample handling apparatus for separating a relatively constant fraction of the exhaust flowing from the engine and for conducting said exhaust fraction to an analyzer;
   diluent adding means for doping said exhaust fraction with a diluent gas upstream of said analyzer; and
   processor means for receiving said flow signal and for operating said diluent adding means in response to said flow signal.

2. A system according to claim 1, wherein said meter comprises an airflow sensor associated with an electronic engine control for operating a fuel injection system of said engine.

3. A system according to claim 1, wherein said meter comprises a flow meter for measuring the air flowing through an intake manifold associated with said engine.

4. A system according to claim 1, wherein said sample handling apparatus comprises a sample line, a vacuum pump, and a mass flow meter for measuring the flow through said sample line.

5. A system according to claim 4, wherein said mass flow meter is situated upstream from said vacuum pump.

6. A system according to claim 1, wherein said diluent adding means comprises:
   a source of diluent gas;
   a flow meter for measuring the flow of said diluent and for generating a diluent signal which corresponds to the magnitude of said flow; and
   a diluent valve for controlling the flow of diluent gas introduced into said sample handling apparatus, with said valve being operated by said processor in response to said diluent signal and said engine airflow signal.

7. A system according to claim 6, wherein said processor operates said diluent valve such that the fraction of the total engine exhaust flow passing into said analyzer remains at a relatively constant value.

8. A system according to claim 1, wherein said analyzer comprises:
   means for detecting a constituent in the exhaust conveyed to the analyzer by said sample handling apparatus;
   means for generating a constituent signal corresponding to the detected level of said constituent; and
   means for transmitting said constituent signal to said processor.

9. A system for measuring the mass flow of an automotive engine exhaust constituent, comprising:
   a meter for measuring the mass of air flowing through said engine and for generating a flow signal corresponding to said airflow;
   sample handling apparatus for separating a relatively constant fraction of the exhaust flowing from the engine and for conducting said exhaust fraction to an analyzer means;
   analyzer means for detecting a constituent in the exhaust conveyed by said sample handling apparatus, said analyzer means further comprising means for generating a constituent signal corresponding to the detected level of said constituent and means for transmitting said constituent signal to a processor means;
   diluent adding means for doping said exhaust fraction with a diluent gas upstream of said analyzer, with said diluent adding means comprising a source of diluent gas, a flow meter for measuring the flow of said diluent and for generating a diluent signal which corresponds to the magnitude of said flow, and a diluent valve for controlling the diluent flow; and
   processor means for receiving said flow and diluent signals and for operating said diluent valve so that the exhaust flowing into said analyzer remains a constant fraction of the total mass of exhaust flowing from the engine, with said processor means further comprising means for using said constituent signal for determining the mass flow of said constituent in said exhaust.

10. A system for measuring the mass flow of sulfur dioxide in an automotive engine exhaust, comprising:
    a meter for measuring the mass of air flowing through said engine and for generating a flow signal corresponding to said airflow;
    sample handling apparatus for separating a fraction of the exhaust flowing from the engine and for conducting said exhaust fraction to an analyzer means;
    analyzer means for detecting the level of sulfur dioxide in the exhaust conveyed by said sample handling apparatus, said analyzer means comprising:
    means for promoting oxidation of said exhaust fraction;
    detector means for determining the mass of sulfur dioxide per unit volume of exhaust flow;
    means for generating a sulfur dioxide signal corresponding to the detected level of sulfur dioxide; and
    means for transmitting said sulfur dioxide signal to a processor means;
    diluent adding means for doping said exhaust fraction with a diluent gas upstream of said means for promoting oxidation of said exhaust, with said diluent adding means comprising a source of diluent gas, a flow meter for measuring the flow of said diluent and for generating a diluent signal which corresponds to the magnitude of said flow, and a diluent valve for controlling the diluent flow; and
    processor means for receiving said flow and constituent and diluent signals and for operating said diluent valve so that the mass of exhaust flowing into said analyzer remains a constant fraction of the total mass of exhaust flowing from the engine, with said processor means further comprising means for using said constituent signal for determining the mass flow of said constituent in said exhaust.

11. A system according to claim 10, wherein said meter comprises an airflow sensor associated with an electronic engine control for operating a fuel injection system of said engine.

12. A system according to claim 10, wherein said meter comprises a flow meter for measuring the air flowing through an intake manifold associated with said engine.

13. A system according to claim 10, wherein said means for promoting oxidation of said exhaust fraction comprises a heated chamber through which said exhaust passes before moving into a detector within said analyzer.

14. A system according to claim 10, wherein said detector means comprises an electrochemical cell.

15. A system according to claim 14, wherein said detector means further comprises a pump system for automatically controlling the quantity of electrolyte within said electrochemical cell.

16. A system according to claim 14, wherein said detector means further comprises a cooler for controlling the temperature of the electrolyte within said electrochemical cell.

17. A system according to claim 16, wherein said cooler comprises a thermoelectric cooler.

18. A system according to claim 14, wherein said detector means comprises a coulometer.

19. A system according to claim 18, wherein said constituent signal comprises a current signal from said coulometer, with the magnitude of said current signal being proportional to the mass flow of sulfur dioxide in said exhaust.

20. A system according to claim 10, wherein said diluent comprises gaseous oxygen.

21. A method for using an analyzer to determine the amount of lubricating oil consumed by an automotive engine, comprising the steps of:
   a) determining the amount of sulfur dioxide within the room air being drawn into said engine;
   b) maintaining a constant total flow comprised of a constant fraction of the engine's exhaust gas and a diluent gas through said analyzer, while:
      1) determining the amount of sulfur dioxide contained within the engine's exhaust, while adding a known quantity of sulfur dioxide to the engine's intake air supply while the engine is operating; and while
      2) determining the amount of sulfur dioxide contained within the engine's exhaust, while operating the engine on room air;
   c) determining an efficiency factor for said analyzer by comparing the amounts of sulfur dioxide determined in steps c and d; and
   d) using said efficiency factor and the concentration of sulfur in the engine oil and the amounts of sulfur dioxide determined in steps a and d to determine the amount of lubricating oil leaving the engine through its exhaust.

22. A method according to claim 21, wherein said analyzer comprises a coulometer.

* * * * *